(12) United States Patent
Bäckström et al.

(10) Patent No.: US 6,932,962 B1
(45) Date of Patent: Aug. 23, 2005

(54) AEROSOL DRUG FORMULATIONS CONTAINING HYDROFLUOROALKANES AND ALKYL SACCHARIDES

(75) Inventors: Kjell Bäckström, Lund (SE); Magnus Dahlbäck, Lund (SE); Ann Johansson, Lund (SE); Göran Källstrand, Bjärred (SE); Elisabet Lindqvist, Lund (SE)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 08/601,005

(22) PCT Filed: Dec. 19, 1995

(86) PCT No.: PCT/SE95/01542

§ 371 (c)(1),
(2), (4) Date: Mar. 1, 1997

(87) PCT Pub. No.: WO96/19198

PCT Pub. Date: Jun. 27, 1996

(30) Foreign Application Priority Data

Dec. 22, 1994 (SE) .................................... 9404469
Jul. 6, 1995 (SE) .................................... 9502452

(51) Int. Cl.[7] .......................... A61K 9/14; A61K 47/00
(52) U.S. Cl. ........................... 424/46; 424/45; 514/975
(58) Field of Search ........................... 424/45, 46, 489; 514/2, 975

(56) References Cited

U.S. PATENT DOCUMENTS

| | | | |
|---|---|---|---|
| 2,992,645 A | 7/1961 | Fowler | |
| 3,014,844 A | 12/1961 | Thiel et al. ................... 167/82 |
| 3,632,743 A | 1/1972 | Geller et al. .................. 424/45 |
| 3,671,625 A | 6/1972 | Altounyan | |
| 4,232,002 A | 11/1980 | Nogrady ...................... 424/45 |
| 4,450,151 A | 5/1984 | Shinozawa | |
| 4,462,983 A | 7/1984 | Azria | |
| 4,524,769 A | 6/1985 | Wetterlin | |
| 4,534,345 A | 8/1985 | Wetterlin | |
| 4,537,772 A | 8/1985 | Alexander | |
| 4,548,922 A | 10/1985 | Carey et al. .................. 514/4 |
| 4,613,500 A | 9/1986 | Suzuki et al. ................ 429/85 |
| 4,668,218 A | 5/1987 | Virtanen | |
| 4,690,952 A | 9/1987 | Kagatani et al. ............. 514/808 |
| 4,731,360 A | 3/1988 | Alexander | |
| 4,746,508 A | 5/1988 | Carey et al. .................. 424/88 |
| 4,788,221 A | 11/1988 | Kagatani et al. ............. 514/808 |
| 4,794,000 A | 12/1988 | Ecanow ....................... 424/457 |
| 4,847,298 A | 7/1989 | Alexander et al. ........... 514/565 |
| 4,849,405 A | 7/1989 | Ecanow ........................ 514/3 |
| 4,895,719 A | 1/1990 | Radhakrishnan et al. ..... 424/45 |
| 4,900,730 A | 2/1990 | Miyauchi ..................... 514/12 |
| 4,907,583 A | 3/1990 | Wetterlin et al. | |
| 4,926,852 A | 5/1990 | Zoltan et al. | |
| 4,959,358 A | 9/1990 | Carey et al. ................. 514/171 |
| 4,963,367 A | 10/1990 | Ecanow ....................... 424/485 |
| 4,994,439 A | 2/1991 | Longenecker et al. ......... 514/3 |
| 5,006,343 A | 4/1991 | Benson et al. .............. 424/450 |
| 5,011,678 A | 4/1991 | Wang et al. .................. 424/45 |
| 5,118,494 A | 6/1992 | Schultz et al. ............... 424/45 |
| 5,122,127 A | 6/1992 | Stanley | |
| 5,122,376 A | 6/1992 | Aliverti et al. ............. 424/405 |
| 5,179,079 A | 1/1993 | Hansen et al. ................ 514/4 |
| 5,192,548 A | 3/1993 | Velasquez et al. | |
| 5,200,393 A | 4/1993 | Weiner ......................... 514/3 |
| 5,202,129 A | 4/1993 | Samejima et al. .......... 424/489 |
| 5,225,183 A | 7/1993 | Purewal et al. ............... 424/45 |
| 5,254,330 A | 10/1993 | Ganderton et al. | |
| 5,260,306 A | 11/1993 | Boardman et al. | |
| 5,262,150 A | 11/1993 | Laugier et al. | |
| 5,284,656 A | 2/1994 | Platz et al. ................ 424/435 |
| 5,288,498 A | 2/1994 | Stanley et al. | |
| 5,306,483 A | 4/1994 | Mautone ...................... 424/45 |
| 5,320,094 A | 6/1994 | Laube et al. | |
| 5,341,800 A | 8/1994 | Clark et al. | |
| 5,348,730 A | 9/1994 | Greenleaf et al. ............ 424/45 |
| 5,349,947 A | 9/1994 | Newhouse et al. | |
| 5,352,461 A | 10/1994 | Feldstein et al. | |
| 5,354,562 A | 10/1994 | Platz et al. ................ 424/489 |
| 5,364,838 A | 11/1994 | Rubsamen .................... 514/3 |
| 5,376,359 A | 12/1994 | Johnson | |
| 5,376,386 A | 12/1994 | Ganderton et al. | |
| 5,384,133 A | 1/1995 | Boyes et al. | |
| 5,419,315 A | 5/1995 | Rubsamen | |
| 5,431,902 A | 7/1995 | Cuine et al. | |
| 5,437,271 A | 8/1995 | Hodson et al. | |
| 5,451,569 A | 9/1995 | Wong et al. | |
| 5,458,135 A | 10/1995 | Patton et al. | |

(Continued)

FOREIGN PATENT DOCUMENTS

AU  43 556/93  1/1994

(Continued)

OTHER PUBLICATIONS

Allenby et al., "The absorption of Insulin Across the Respiratory Tract of the Guinea-Pig" The Aerosol Society, Fourth Annual Conference, University of Surrey, Apr. 9-11, 1990.

(Continued)

*Primary Examiner*—S. Mark Clardy
*Assistant Examiner*—Frank I. Choi
(74) *Attorney, Agent, or Firm*—Fish & Richardson P.C.

(57) ABSTRACT

Aerosol formulations suitable for use in pressurised metered dose inhalers comprise a hydrofluoroalkane propellant, an medicament for inhalation and a surfactant which is a a $C_8$–$C_{16}$ fatty acid or salt thereof, a bile salt, a phospholipid, or an alkyl saccharide.

53 Claims, No Drawings

U.S. PATENT DOCUMENTS

| | | | |
|---|---|---|---|
| 5,474,759 A | 12/1995 | Fassberg et al. | |
| 5,482,032 A | 1/1996 | Smith et al. | |
| 5,482,706 A | 1/1996 | Igari et al. | |
| 5,506,203 A | 4/1996 | Backstrom et al. | 514/4 |
| 5,514,670 A | 5/1996 | Friedman et al. | 514/2 |
| 5,518,998 A | 5/1996 | Backstrom et al. | 514/3 |
| 5,607,915 A | 3/1997 | Patton | 514/12 |
| 5,658,878 A | 8/1997 | Bäckström et al. | |
| 5,661,130 A * | 8/1997 | Meezan et al. | 514/25 |
| 5,674,471 A * | 10/1997 | Akehurst et al. | 424/45 |
| 5,676,931 A * | 10/1997 | Adjei et al. | |
| 5,688,782 A * | 11/1997 | Neale et al. | 514/180 |
| 5,695,743 A * | 12/1997 | Purewal et al. | |
| 5,707,644 A | 1/1998 | Illum | |
| 5,730,969 A | 3/1998 | Hora et al. | 424/85 |
| 5,747,445 A | 5/1998 | Bäckström et al. | |
| 5,814,607 A | 9/1998 | Patton | 514/12 |
| 5,830,853 A | 11/1998 | Bäckström et al. | |
| 5,837,699 A * | 11/1998 | Sequeira et al. | 514/169 |
| 5,858,968 A | 1/1999 | Weiner et al. | |
| 5,952,008 A | 9/1999 | Bäckström et al. | |
| 5,997,848 A | 12/1999 | Patton et al. | |
| 6,004,574 A * | 12/1999 | Backström | |
| 6,039,932 A * | 3/2000 | Govind et al. | |
| 6,051,256 A | 4/2000 | Platz et al. | |
| 6,165,976 A * | 12/2000 | Backström | |
| 6,306,440 B1 | 10/2001 | Bäckström et al. | |
| 6,413,497 B1 | 7/2002 | Weil et al. | |
| 6,419,899 B1 | 7/2002 | Weil et al. | |
| 6,524,557 B1 * | 2/2003 | Backstrom et al. | 424/46 |
| 2002/0071812 A1 | 6/2002 | Weil et al. | |
| 2004/0028618 A1 | 2/2004 | Weil et al. | |

FOREIGN PATENT DOCUMENTS

| | | |
|---|---|---|
| CA | 2075060 | 1/1991 |
| CA | 2075058 | 8/1991 |
| CN | 1067579 A | 6/1993 |
| DE | 1 208 036 | 11/1963 |
| DE | 26 20 446.6 | 5/1976 |
| DE | 25 03 962 A1 | 8/1976 |
| DE | 26 20 483 | 12/1976 |
| DE | 29 26 095 A1 | 3/1980 |
| DE | 261 096 A1 | 5/1983 |
| EP | 0 023 359 A2 | 7/1980 |
| EP | 0 055 041 | 12/1981 |
| EP | 0 130 550 | 6/1984 |
| EP | 0 133 252 | 7/1984 |
| EP | 0 122 036 | 10/1984 |
| EP | 0 128 831 | 12/1984 |
| EP | 0 200 383 | 4/1986 |
| EP | 0 225 189 | 11/1986 |
| EP | 0 312 052 A1 | 10/1987 |
| EP | 0 275 404 A1 | 11/1987 |
| EP | 0 272 097 | 12/1987 |
| EP | 0 364 235 A1 | 4/1988 |
| EP | 0 272 097 | 6/1988 |
| EP | 0 372 777 | 6/1988 |
| EP | 0 360 340 | 9/1989 |
| EP | 0 372 777 A2 | 11/1989 |
| EP | 0 372 777 A3 | 11/1989 |
| EP | 0 499 344 A2 | 11/1989 |
| EP | 0 360 340 A1 | 3/1990 |
| EP | 0 478 456 A1 | 9/1991 |
| EP | 0 455 463 | 11/1991 |
| EP | 0 504 112 A2 | 3/1992 |
| EP | 0 504 112 A3 | 3/1992 |
| EP | 0 518 600 A1 | 6/1992 |
| EP | 0 518 601 A1 | 6/1992 |
| EP | 0 518 600 A1 | 12/1992 |
| EP | 0 626 173 A1 | 5/1994 |
| EP | 0 383 751 | 9/1994 |
| FR | 76 36431 | 12/1976 |
| GB | 837465 | 6/1960 |
| GB | 1 242 211 | 8/1971 |
| GB | 1 520 247 | 8/1978 |
| GB | 1 527 605 | 10/1978 |
| GB | 1 569 611 | 6/1980 |
| IE | 920826 | 9/1992 |
| JP | 55-361 | 1/1980 |
| JP | 632 932 | 1/1988 |
| JP | 1 117 825 | 5/1989 |
| JP | 4 041 421 | 2/1992 |
| JP | 4 149 126 | 5/1992 |
| SE | 8 807 820 | 11/1986 |
| SE | 8007820-7 | 11/1986 |
| SE | 9400371-2 | 2/1994 |
| SE | 9302198-8 | 5/1994 |
| WO | WO 87/05213 A1 | 9/1987 |
| WO | 88/09163 | 12/1988 |
| WO | WO 90/04962 | 5/1990 |
| WO | 90/07333 | 7/1990 |
| WO | WO 91/04011 | 4/1991 |
| WO | WO 91/11495 | 8/1991 |
| WO | WO 91/11496 | 8/1991 |
| WO | WO 91/14422 | 10/1991 |
| WO | WO 91/16038 | 10/1991 |
| WO | WO 91/16882 | 11/1991 |
| WO | WO 91/16929 | 11/1991 |
| WO | WO 91/18091 A1 | 11/1991 |
| WO | WO 92/04069 | 3/1992 |
| WO | WO 92/06704 | 4/1992 |
| WO | WO 92/08446 | 5/1992 |
| WO | WO 92/22286 | 12/1992 |
| WO | WO 92/22287 | 12/1992 |
| WO | WO 92/22288 | 12/1992 |
| WO | WO 93/25198 | 12/1993 |
| WO | WO 94/07514 | 4/1994 |
| WO | WO 94/22461 | 10/1994 |
| WO | WO 95/00128 | 1/1995 |
| WO | WO 95/00151 | 1/1995 |
| WO | WO 96/06598 | 3/1996 |
| WO | WO 96/18384 | 6/1996 |
| WO | WO 96/19206 | 6/1996 |
| WO | WO 96/19207 | 6/1996 |
| WO | WO 97/10850 | 3/1997 |

OTHER PUBLICATIONS

Aungst et al., "Comparison of the effects of various transmucosal absorption promoters of buccal insulin delivery" Int. J. Pharm. (Netherlands) 53(3):227-235, 1989.

Bjork, "Starch Microspheres as a Nasal Delivery System for Drugs" ACTA Universitatis Upsaliensis 103, 1993.

Bjork et al., "Degradable starch microspheres as a naval delivery system for insulin" Int. J. Pharm 47:233-238, 1988.

Chandler et al., "Nasal absorption in rats. II Effect of enhancers on insulin absorption and nasal histology" Int. J. Pharm 76:61-70, 1991.

Cutie et al., "The Role of Dispersing Agents in Inhalation and Intranasal Aerosol Suspensions" Aerosol Age, pp. 52-54, 1985.

Damasy et al., "Intranasal Insulin" Diabetes Res. and Clin. Pract. 5:S163, 1988.

Edman et al., "Routes of Delivery: Case Studies:Nasal Delivery of Peptide Drugs" Advanced Drug Del. Rev. 8: 165-177, 1992.

Gordon et al., "Nasal absorption of insulin: Enhancement by hydrophobic bile salts" Proc. Natl. Acad. Sci. 32:7419-7423, 1985.

Hirai et al., "Effect of Surfactants on the Nasal Absorption of Insulin in Rats" Int. J. Pharm. 9:165-172, 1981.

Igawa et al., "Effect of Absorption Promoters in Intranasal

Administration of Human Fibroblast Interferon . ." Chem Pharm. Bull. 37:418-421, 1989.

Komada et al., "Intratracheal Delivery of Peptide and Protein Agents: Absorption from Solution and Dry Powder by Rat Lung" J. Pharm. Sciences 83:863, 1994.

Lee et al., "Mucosal Penetration Enhancers for Facilitation of Peptide and Protein Drug Absorption" Crit. Rev. Therapeutic Drug Carrier Systems 8(2):91-192, 1991.

Lee et al., "Intranasal Biovailability of insulin Powder Formulations: . . . " J. Pharm. Sciences 80(8):725, 1991.

Mishima et al., "Studies on the Promoting Effects of Medium Chain Fatty Acid Salts on the Nasal Absorption. ." J. Pharma. Dyn. 10:624-631, 1987.

Morita et al., "Effects of Various Absorption Promoters on Pulmonary Absorption of Drugs . . . " Biol. Pharm. Bull. 16:269-262, 1993.

Moses et al., "Insulin Administered Intranasally as an Insulin-Bile Salt Aerosol" Diabetes 32:1040, 1983.

Olanoff et al., "Method to Enhance Intranasal Peptide Delivery" American Chemical Society Symposium, Lee & Good, eds., New York, Apr. 13-18, 1986.

Pontiroli et al., "Nasal administration of glucagon and human calcitonin to healthy subjects: a comparison of powders . . . " Eur. J. Clin. Pharmacol. 37:427-430, 1989.

SanGiovanni, "Just how practical is aerosolized nasal insulin" Spray Tech. & Marketing 2(1):16-19, 1992.

Schipper et al., "Nasal Insulin Delivery with Dimethyl-B-Cyclodextrin as an Absorption Enhancer in Rabbits. . " Pharm. Res. 10:682, 1993.

Touitou et al., "Targeted Enteral Delivery of Insulin to Rats" Int. J. Pharm. (AMST) 30:95-100, 1986.

Wearley, "Recent Progress in Protein and Peptide Delivery by Noninvasive Routes" Crit. Rev. in Therapeutic Drug Carrier Systems 8(4):331-394, 1991.

Wigley et al., "Insulin Across Respiratory Mucosae by Aerosol Delivery" Diabetes 20(8):552, 1971.

Yoshida et al., "Absorption of Insulin Delivered to Rabbit Trachea Using Aerosol Dosage Form" J. of Pharm. Sciences 68:670, 1979.

Zinman, "The physiologic replacement of insulin" Medical Intelligence: Drug Therapy 321:363, 1989.

Chinese Medicinal Chemistry, 25(9):421-423, 1994 (English Translation provided).

Almer et al. "Insulin Inhalation—At Last A Breakthrough, "Diabetes Res. And Clin. Pract., 5:s.163 (1988).

Aungst and Rogers, "Comparison of the Effects of Various Transmucosal Absorption Promoters on Buccal Insulin Delivery,"Int. J. Pharm. (Netherlands), 53/3, 227-235 (1989).

Björk et al., "Characterization of degradable starch . . . "International Journal of Pharmaceutics, 62 (1990) 187-192.

Brange et al., "Monomeric Insulins and Their Experimental and Clinical Implications,"Diabetes Care, 13:923-954 (1990).

Byron et al., "Drug Delivery via the Respiratory . . . ,"Journal of Aerosol Medicine, 7:49-75 (1994).

Chien et al., "Intranasal Drug Delivery for Systemic Medications,"CRC Critical Reviews in Therapeutic Drug Carrier Systems, 4:67-194 (1987).

Chien et al., "Potential Developments in Systemic Delivery of Insulin,"Drug Development and Industrial Pharmacy, 15(10), 1601-1634 (1989).

Colthorpe et al., "The Pharmacokinetics of Pulmonary-Delivered Insulin: A Comparison of Intratracheal . . . ,"Pharmaceutical Research, vol. 9, No. 6, pp. 764-769 (1992).

Dahlbäck et al., "Deposition of Tracer Aerosols in the Rabbit Respiratory Tract,"Journal of Aerosol Science, vol. 18, No. 6, pp. 733-736 (1987).

Dahlbäck et al., "Regional Administration of Drugs to the Rabbit Respiratory Tract. Effects on Absorption,"Journal of Aerosol Medicine, 1:222-223 (1988).

Dempster et al., Anabolic Actions of Parathyroid Hormone on Bone, Endocrine Reviews 14:690-709, (1993).

"Diabetes Mellitus", Ch. VI in Scientific American Medicine, Scientific American, Inc., Apr. 1993.

The Diabetes Control and Complications Trial Research Group, "The Effect of Intensive Treatment of Diabetes on the Development . . . Complications in Insulin-Dependent Diabetes Mellitus," New England Journal of Medicine, 329:977-986 (1993).

Elliott et al., "Parenteral absorption of insulin . . .,"Austr. Paediatr. J., 23:293-297 (1987).

Eppstein and Longenecker, "Alternative Delivery Systems for Peptides and Proteins As Drugs,"CRC Critical Reviews in Therapeutic Drug Carrier Systems, 5:99-139 (1988).

Goni et al., "Palmitoylcarnitine, a surface-active metabolite, "FEBS Lett., vol. 390, pp. 1-5 (1996).

Hoover et al., "Peptides are Better Absorbed from the Lung than the Gut in the Rat,"Pharmaceutical Research, vol. 9, No. 8, pp. 1103-1106 (1992).

Jacobs, Maarten A.J.M., "The Pharmacodynamics and Activity of Intranasally Administered Insulin in Healthy Male Volunteers,"Diabetes, vol. 42, pp. 1649-1655 (1993).

Jaegfeldt, H. et al., "Particle size distribution from different modifications of Turbuhaler®," Proceedings of an international workshop on a new inhaler, May 21-22, 1987 (London) pp. 90-99.

Jones, "Pulmonary absorption of insulin", (1998) Ph.D. Thesis, Welsh School of Pharmacy, University of Wales, United Kingdom.

Köhler, Dieter, "Aerosols for Systemic Treatment,"Lung, Supplement: 677-684 (1990).

Köhler et al., "Nicht radioaktives Verfahren zur Messung der Lungenpermeabilitat: Inhalation von Insulin,"Aten-w-Lungenkrkh, Jahrgang 13, Nr. Jun. 1987; 230-232.

Lasker, "The Diabetes Control and Complications Trial, "The New England Journal of Medicine, 329:1035-1036 (1993).

Laube et al., "Preliminary of the Efficacy of Insulin Aerosol Delivery by Oral Inhalation in Diabetic Patients,"Journal of the American Medical Association, 239:2106-2109 (1993).

Lecluyse et al., "In Vitro Effects of Long-Chain Acylcarnitines on the Permeability, Transepithelial Electrical Resistance and Morphology of Rat Colonic Mucosa,"J. Pharmacol. Exp. Ther., vol. 265(2), pp. 955-962 (1993).

Lee et al., "Development of an aerosol dosage form containing insulin,"Journal of Pharmaceutical Sciences, vol. 65, No. 4, pp. 567-574 (1976).

Li, Yuping et al., "Effect of a Conjugated Bile Salt on the Pulmonary Absorption of Insulin in Rats,"Eur. J. Pharm. Biopharm., vol. 39, pp. 216-221 (1993).

Liu et al., "Pulmonary Delivery of Free . . . ,"Pharmaceutical Research, 10:228-232 (1993).

Longenecker et al., "Effects of Sodium Taurodihydrofusidate on Nasal Absorption of Insulin in Sheep,"J. Pharm. Sci., 76(5):351-355 (1987).

Mizgala et al., "Renal Handling of Phosphate,"Physiological Reviews, 65(2): 431-466 (1985).

Nagai et al., "Powder Dosage Form of Insulin for Nasal Administration,"*J. Controlled Release*, 1:15-22 (1984).

Nagano et al., "New Method of Insulin . . .,"*Jikeikai Medical Journal*, 32: 503-506 (1985).

Newman, "Chapter 9: Therapeutic aerosols", In: *Aerosols and the Lung: Clinical and Experimental Aspects*, (1984) Butterworth & Co., United Kingdom.

O'Hagan and Illum, "Absorption of Peptides and Proteins from the Respiratory Tract and the Potential for Development of Locally Administered Vaccine,"*Critical Reviews in Therapeutic Drug Carrier Sys*, 7:35-97 (1990).

Okumura et al., "Intratracheal delivery of insulin absorption from solution and acrosol by rat lung,"*International Journal of Pharmaceutics*, vol. 88, pp. 63-73 (1992).

Olanoff et al., "Method to Enhance Intranasal Peptide Delivery," in "Controlled-Release Technology Pharmaceutical Applications", Lee et al., American Chemical Society, 301-309 (1987).

Patton et al., "Bioavailability of Pulmonary Delivered Peptides and Proteins: α-interferon, Calcitonins and Parathyroid Hormones,"*Journal of Controlled Release*, 28: 79-85 (1994).

Patton et al., "(D) Routes of Delivery: Case Studies, "*Advanced Drug Delivery Reviews*, vol. 8, pp. 179-196 (1992).

Reeve et al., Anabolic Effect of Human Parathyroid Hormone Fragment on Trabecular Bone in Involutional Osteoporosis: A Multicentre Trial, British Medical Journal, pp. 1340-1344, (1980).

*Remington's Pharmaceutical Science*, 18th edition., p. 1079 (1990).

Ruin, "Diabetics May Not Need Their Insulin Shots," article in Sydsvenska (Dagbladet), Monday, Jun. 12, 1989.

Sakr., "A new approach for insulin . . . ,"*International Journal of Pharmaceutics*, 86:1-7 (1992).

Salzman et al., "Intranasal Aerosolized Insulin Mixed-Meal Studies and Long-term Use in Type 1 Diabetes,"*The New England Journal of Medicine*, 1312:1078-1084 (1985).

Schanker et al., "Species Comparison of Drug Absorption from the Lung Aerosol Inhalation or Intratracheal Injection, "*Drug Metabolism & Disposition*, vol. 14, pp. 79-88 (1986).

Schluter et al., "Pulmonary Administration . . . Type 1 Diabetes" Abstract #298, *Diabetes*, 33 (Supplement): 75A (1984).

Selam and Charles, "Devices for Insulin Administration, "*Diabetes Care*, 13:955-979 (1990).

Timsina et al., "Drug Delivery to the Respiratory Tract Using Dry Powder Inhalers,"*Int. J. Pharmaceutics*, 101:1-13 (1994).

Wang et al., *Parenteral Science and Technology*, 42 (2S), S4-S26, 1988.

Wetterlin, Kiell, "Turbuhaler: A New Powder Inhaler for Administration of Drugs to the Airways,"*Pharmaceutical Research*, vol. 5, pp. 506-508, (1988).

Wigley et al., "Insulin Across Respiratory Mucosae by Aerosol Delivery,"*Diabetes*, 20:552-556 (1971).

Yamamoto et al., "Absorption Enhancement of Intrapulmonary Administered Insulin by Various Absorption . . . ,"*J. Pharm. Pharmacol.*, vol. 46, pp. 14-18 (1994).

Zingg et al., "Transhepatic Absorption and Biliary Excretion of Insulin,"*Can. J. Physiol. Pharmacol.*, 65:1982-1987 (1987).

Byron, "Aerosol Formulation, Generation, and Delivery Using Metered Systems,"*Respiratory Drug Delivery*, pp. 167-205 (1990).

Dalby et al., "CFC Propellant Substitution: P-134a as a Potential Replacement for P-12 in MDIs,"*Pharmaceutical Technology*, pp. 26-29 (1990).

European Pharmacopoeia 4.5, pp. 3747-3748.

Handbook of Pharmaceutical Excipients, 3rd Edition, pp. 70-72, 356-357, and 608-609 (2000).

Kontny et al., "Issues Surrounding MDI Formulation Development with Non-CFC Propellants,"*J. of Aerosol Medicine*, 4:181-187 (1991).

Merck Index, 2nd Edition, p. 1171 (1996).

Miller, "The Effects of Water in Inhalation Suspension Aerosol Formulations,"*Respiratory Drug Delivery*, pp. 249-257 (1990).

Remington's Pharmaceutical Sciences, 17th Edition, pp. 773-774, 1301 and 1310-1311 (1985).

Sciarra et al., "Pharmaceutical Aerosols,"*The Theory and Practice of Industrial Pharmacy*, pp. 589-592 (1986).

Ullman's Encyclopedia of Industrial Chemistry, 5th Edition, A16:361-374 (1990).

XP-002181798.

* cited by examiner

AEROSOL DRUG FORMULATIONS CONTAINING HYDROFLUOROALKANES AND ALKYL SACCHARIDES

CROSS REFERENCE TO RELATED APPLICATIONS

This application is a 371 of PCT/SE95/01542 filed on Dec. 19, 1995.

FIELD OF THE INVENTION

The present invention relates to aerosol formulations suitable for use in pressurised metered dose inhalers (pMDI's). More particularly, it relates to a formulation including a hydrofluoroalkane (HFA) propellant and a particularly suitable surface active-dispersing agent.

BACKGROUND OF THE INVENTION

Medicaments for treating respiratory and nasal disorders are frequently administered in aerosol formulations through the mouth or nose. One widely used method for dispensing such an aerosol formulation involves making a suspension formulation of the medicament as a finely divided powder in a liquefied gas known as a propellant. Pressurised metered dose inhalers, or (pMDI's) are normally used to dispense such formulations to a patient. Surface active agents, or surfactants, are commonly included in order to aid dispersion of the medicament in the propellant and to prevent aggregation of the micronised medicament particles, and to improve lubrication of the valve.

Until recently, chlorofluorocarbon-containing propellants (CFC's) were accepted for use in all pharmaceutical aerosol formulations. Typical surfactant dispersing agents used in the CFC formulations were for example sorbitantrioleate, oleic acid, lecithines, and ethanol. Since CFC's have been implicated in the destruction of the ozone layer, a new generation of propellants has emerged to take their place.

Hydrofluoroalkane (HFA) propellants for example 1,1,1,2-tetrafluoroethane (P134a), 1,1,1,2,3,3,3-heptafluoropropane (P227) and 1,1-difluoroethane (P152a) are today considered to be the most promising new propellants. Not only are they environmentally acceptable, but they also have low toxicity and vapour pressures suitable for use in aerosols. However, the surfactants commonly used with the CFC formulations are not necessarily suitable for use with the new generation of propellants. Various alternative surfactants have been proposed.

For example, WO 92/00061 discloses polyethoxylated surfactant for use with hydrofluorocarbon propellants. WO 91/11173 discloses fluorinated surfactants. WO 91/14422 discloses perfluorinated carboxylic acid propellants for use with hydrofluorocarbon propellants. WO 92/00107 discloses the use of a 1,1,1,2-tetrafluoroethane-soluble surfactant with 1,1,1,2-tetrafluoroethane propellant.

SUMMARY OF THE INVENTION

It has now been found that certain specific classes of surfactant are particularly suitable for use with the new generation of propellant.

Accordingly, the present invention provides a pharmaceutical aerosol formulation comprising a hydrofluoroalkane propellant or a mixture of hydrofluoroalkane propellants, a physiologically effective amount of a medicament for inhalation and a surfactant selected from a $C_8$–$C_{16}$ fatty acid or salt thereof, a bile salt, a phospholipid or an alkyl saccharide.

The surfactants employed in the present invention give fine dispersions in the new propellants, with good stability. The inventive formulations are therefore useful for administering inhalable medicaments.

Of the fatty acid surfactants and salts thereof, $C_8$–$C_{16}$ fatty acids salts are preferred. Examples of preferred fatty acid salts are sodium, potassium and lysine salts of caprylate ($C_8$), caprate ($C_{10}$), laurate ($C_{12}$) and myristate ($C_{14}$). As the nature of the counterion is not of special significance, any of the salts of the fatty acids are potentially useful. A particularly preferred fatty acid salt is sodium caprate.

Suitable bile salts may be for example salts of cholic acid, chenodeoxycholic acid, glycocholic acid, taurocholic acid, glycochenodeoxycholic acid, taurochenodeoxycholic acid, deoxycholic acid, glycodeoxycholic acid, taurodeoxycholic acid, lithocholic acid, and ursodeoxycholic acid.

Of the bile salts, trihydroxy bile salts are preferred. More preferred are the salts of cholic, glycocholic and taurocholic acids, especially the sodium and potassium salts thereof. The most preferred bile salt is sodium taurocholate.

Suitable phospholipids may be for example single-chain phospholipids, for example lysophosphatidylcholines, lysophosphatidylglycerols, lysophosphatidylethanolamines, lysophosphatidylinositols and lysophosphatidylserines or double-chain phospholipids, for example diacylphosphatidylcholines, diacylphosphatidylglycerols, diacylphosphatidylethanolamines, diacylphosphatidylinositols and diacylphosphatidylserines.

Of the phospholipids, diacylphosphatidylglycerols and diacylphosphatidylcholines are preferred, for example dioctanoylphosphatidylglycerol and dioctanoylphosphatidylcholine.

Suitable alkyl saccharides may be for example alkyl glucosides or alkyl maltosides, for example decyl glucoside and dodecyl maltoside.

The most preferred surfactants are bile salts.

The propellant may comprise for example one or more of 1,1,1,2-tetrafluoroethane (P134a), 1,1,1,2,3,3,3-heptafluoropropane (P227) and 1,1-difluoroethane (P152a), optionally in admixture with one or more other propellants. Prefereably the propellant comprises 1,1,1,2-tetrafluoroethane (P134a) or 1,1,1,2,3,3,3-heptafluoropropane (P227), or a mixture of P134a and P227, for example a density-matched mixture of P134a and P227.

In addition to medicament, propellant and surfactant, a small amount of ethanol (normally up to 5% but possibly up to 20%, by weight) may be included in the formulations of the present invention. Ethanol is commonly included in aerosol compositions as it can improve the function of the metering valve and in some cases also improve the stability of the dispersion.

Medicaments suitable for inclusion in the formulation of the present invention are any which may be delivered by inhalation. Suitable inhalable medicaments may include for example β2-adrenoreceptor agonists for example salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators for example ipratropium bromide and the like; glucocorticosteroids for example beclomethasone, fluticasone, budesonide, tipredane, dexamethasone, betamethasone, fluocinolone, triamcinolone acetonide, mometasone, and the like, and their pharmacologically acceptable esters and salts;

anti-allergic medicaments for example sodium cromoglycate and nedocromil sodium; expectorants; mucolytics; antihistamines; cyclooxygenase inhibitors; leukotriene synthesis inhibitors; leukotriene antagonists, phospholipase-A2 (PLA2) inhibitors, platelet aggregating factor (PAF) antagonists and prophylactics of asthma; antiarrhythmic medicaments, tranquilisers, cardiac glycosides, hormones, antihypertensive medicaments, antidiabetic- antiparasitic- and anticancer- medicaments, sedatives and analgesic medicaments, antibiotics, antirheumatic medicaments, immunotherapies, antifungal and antihypotension medicaments, vaccines, antiviral medicaments, proteins, peptides, vitamins and others, for example cell surface receptor blockers, antioxidants, free radical scavengers and organic salts of N,N'-diacetylcystine.

Combinations of medicaments are also suitable, for example a combination of formoterol and budesonide.

The medicaments may be used in the form of salts or esters or solvates (hydrates), where appropriate.

Other ingredients may be added into the formulation of the present invention, if desired. Such ingredients may be for example other pharmaceutically active agents, adjuvants, carriers, flavouring agents, buffers, antioxidants, chemical stabilisers and the like.

Preferably the surfactant and medicament are present in the present invention in a ratio of approximately 1:50 to 1:0.2. The preferred concentration of medicament in the formulations of the present invention is 0.1 mg/ml to 25 mg/ml.

"A medicament for inhalation" means a medicament which is suitable for inhalation and which consists largely of particles in a size range appropriate for maximal deposition in the lower respiratory tract (i.e., under 10 microns). Therefore as much as possible of the medicament preferably consists of particles having a diameter of less than 10 microns, for example 0.01–10 microns or 0.1–6 microns, for example 0.1–5 microns. Preferably at least 50% of the medicament consists of particles within the desired size range. For example at least 60%, preferably at least 70%, more preferably at least 80% and most preferably at least 90% of the medicament consists of particles within the desired size range.

Therefore, the medicament for use in the present invention may have to be processsed prior to inclusion in the formulations, in order to produce particles in the desired size range. For example the medicament may be micronised, for example out in a suitable mill, for example a jet mill. Alternatively, particles in the desired particle range may be obtained by for example spray drying or controlled crystallisation methods, for example crystallisation using supercritical fluids.

Preferably, the surfactant for use in the present invention is also in the desired particle size range.

Where the surfactant and medicament are both micronised, they may be dry mixed and then micronised together, or they may be micronised separately and then mixed. The propellant and optional ethanol may be added thereafter, in one or more than one step.

Alternatively a portion of the micronised surfactant may be cold-mixed with a portion of the propellant and optional ethanol, whereafter the micronised medicament may be added. After mixing in of the medicament the remaining surfactant and propellant and optional ethanol may be added and the suspension filled into appropriate containers.

The aerosol formulation of the present invention is useful for the local or systemic treatment of diseases and may be administered for example via the upper and lower respiratory tract, including by the nasal route. As such the present invention also provides said aerosol formulation for use in therapy; the use of the aerosol formulation in the manufacture of a medicament for the treatment of diseases via the respiratory tract; and a method for the treatment of a patient in need of therapy, comprising administering to said patient a therapeutically effective amount of the aerosol formulation of the present invention.

The following Examples are intended to illustrate, but not limit, the invention:

Formulations of various medicaments in P134a and/or P227 with different surfactants were prepared in order to assess the quality of the suspensions formed. In the following examples the quality of the suspension is rated as "acceptable" or "good". An acceptable suspension is characterised by one or more of slow settling or separation, ready re-dispersion, little flocculation, and absence of crystallisation or morphology changes, such that the dispersion is sufficiently stable to give a uniform dosing. A good dispersion is even more stable.

EXAMPLE 1

Micronised formoterol fumarate (1 part) and micronised sodium taurocholate (2 parts) (total 5 mg) were added to a plastic coated glass bottle. The bottle was chilled to approximately 40° C. with a mixture of carbon dioxide ice and isopropanol, and 10 ml chilled P134a (at approximately 40° C.) was added. The bottle was sealed with a metering valve and treated in an ultrasonic bath for about 10 minutes.

A good suspension formed.

EXAMPLE 2

Micronised budesonide (10 parts) and micronised sodium taurocholate (2 parts) (total 5 mg) were added to a plastic coated glass bottle. The bottle was chilled to approximately 40° C. with a mixture of carbon dioxide ice and isopropanol, and 10 ml chilled P134a (at approximately 40° C.) was added. The bottle was sealed with a metering valve and treated in an ultrasonic bath for about 10 minutes.

A good suspension formed.

EXAMPLE 3

Micronised salbutamol sulphate (10 parts) and micronised sodium taurocholate (2 parts) (total 5 mg) were added to a plastic coated glass bottle. The bottle was chilled to approximately 40° C. with a mixture of carbon dioxide ice and isopropanol, and 10 ml chilled P134a (at approximately −40° C.) was added. The bottle was sealed with a metering valve and treated in an ultrasonic bath for about 10 minutes.

A good suspension formed.

EXAMPLE 4

Micronised ipratropium bromide (1 part) and micronised sodium taurocholate (2 parts) (total 5 mg) were added to a plastic coated glass bottle. The bottle was chilled to approximately 40° C. with a mixture of carbon dioxide ice and isopropanol, and 10 ml chilled P134a (at approximately 40° C.) was added. The bottle was sealed with a metering valve and treated in an ultrasonic bath for about 10 minutes.

A good suspension formed.

EXAMPLES 5–8

Examples 1–4 were repeated, substituting propellant P227 for P134a. In all cases, good suspensions formed.

EXAMPLES 9–16

Examples 1–8 were repeated with the following addition: ethanol, approximately 650 µl, was added to the chilled bottle before sealing with the metering valve. In all cases, acceptable suspensions formed.

What is claimed is:

1. A pharmaceutical aerosol formulation comprising a hydrofluoroalkane (HFA) propellant; a physiologically effective amount of a medicament for inhalation; and an alkyl saccharide surfactant, wherein the medicament and the surfactant are suspended in the propellant as a finely divided powder.

2. A pharmaceutical aerosol formulation as claimed in claim 1, wherein the surfactant is selected from the group consisting of an alkyl glucoside and an alkyl maltoside.

3. A pharmaceutical aerosol formulation as claimed in claim 2, wherein the surfactant is selected from the group consisting of decyl glucoside and dodecyl maltoside.

4. A pharmaceutical aerosol formulation as claimed in claim 1, wherein the formulation comprises a propellant selected from the group consisting of 1,1,1,2-tetrafluoroethane (P134a), 1,1,1,2,3,3,3-heptafluoropropane (P227), or 1,1-difluoroethane (P152a).

5. The pharmaceutical aerosol formulation as claimed in claim 4, wherein the surfactant is decyl glucoside.

6. The pharmaceutical aerosol formulation as claimed in claim 4, wherein the surfactant is dodecyl maltoside.

7. A pharmaceutical aerosol formulation as claimed in claim 4, wherein the formulation comprises a propellant mixture comprising 1,1,1,2-tetrafluoroethane (P134a) and 1,1,1,2,3,3,3-heptafluoropropane (P227).

8. A pharmaceutical aerosol formulation as claimed in claim 7, wherein the formulation comprises a density-matched propellant mixture of 1,1,1,2-tetrafluoroethane (P134a) and 1,1,1,2,3,3,3-heptafluoropropane (P227).

9. The pharmaceutical aerosol formulation as claimed in claim 7, wherein the surfactant is decyl glucoside.

10. The pharmaceutical aerosol formulation as claimed in claim 7, wherein the surfactant is dodecyl maltoside.

11. A pharmaceutical aerosol formulation as claimed in claim 1, wherein the medicament is selected from the group consisting of a β2-adrenoreceptor agonist, an anticholinergic bronchodilator, and a glucocorticosteroid.

12. A pharmaceutical aerosol formulation as claimed in claim 1, wherein the medicament is selected from the group consisting of salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, mabuterol, ipratropium bromide, beclomethasone, fluticasone, budesonide, tipredane, dexamethasone, betamethasone, fluocinolone, triamcinolone acetonide, mometasone, and pharmacologically acceptable esters and salts thereof.

13. A pharmaceutical aerosol formulation as claimed in claim 1, wherein the medicament is selected from the group consisting of anti-allergic medicaments, expectorants, mucolytics, antihistamines, cyclooxygenase inhibitors, leukotriene synthesis inhibitors, leukotriene antagonists, phospholipase-A2 (PLA2) inhibitors, platelet aggregating factor (PAF) antagonists, prophylactics of asthma, antiarrhythmic medicaments, tranquilisers, cardiac glycosides, hormones, anti-hypertensive medicaments, antidiabetic medicaments, antiparasitic medicaments, anticancer medicaments, sedatives, analgesic medicaments, antibiotics, antirheumatic medicaments, immunotherapeutic agents, antifungal medicaments, antihypotension medicaments, vaccines, antiviral medicaments, proteins, peptides, vitamins, cell surface receptor blockers, antioxidants, free radical scavengers, and organic salts of N,N'-diacetylcystine.

14. A pharmaceutical aerosol formulation as claimed in claim 1, including ethanol in an amount of up to 20% by weight of propellant and surfactant.

15. A pharmaceutical aerosol formulation as claimed in claim 1, including ethanol in an amount of up to 5% by weight of propellant and surfactant.

16. A pharmaceutical aerosol formulation as claimed in claim 1, further comprising a substance selected from the group consisting of adjuvants, carriers, flavouring agents, buffers, antioxidants and chemical stabilisers.

17. A pharmaceutical aerosol formulation as claimed in claim 1, wherein at least 50% of the medicament consists of particles having a diameter of 0.01–10 microns.

18. A pharmaceutical aerosol formulation as claimed in claim 17, wherein at least 70% of the medicament consists of particles having a diameter of 0.01–10 microns.

19. A pharmaceutical aerosol formulation as claimed in claim 17, wherein at least 90% of the medicament consists of particles having a diameter of 0.01–10 microns.

20. A pharmaceutical aerosol formulation as claimed in claim 1, wherein at least 50% of the medicament consists of particles having a diameter of 0.1–6 microns.

21. A pharmaceutical aerosol formulation as claimed in claim 20, wherein at least 70% of the medicament consists of particles having a diameter of 0.01–6 microns.

22. A pharmaceutical aerosol formulation as claimed in claim 20, wherein at least 90% of the medicament consists of particles having a diameter of 0.01–6 microns.

23. A pharmaceutical aerosol formulation as claimed in claim 1, wherein at least 50% of the medicament consists of particles having a diameter of 0.1–5 microns.

24. A pharmaceutical aerosol formulation as claimed in claim 1, wherein the concentration of medicament in the formulation is 0.1 mg/ml to 25 mg/ml.

25. A pharmaceutical aerosol formulation as claimed in claim 1, wherein the ratio of surfactant to medicament is in the range of 1:50 to 1:0.2.

26. A pharmaceutical aerosol formulation as claimed in claim 1, the formulation comprising a physiologically effective amount of each of a β2-adrenoreceptor agonist and a glucocorticosteriod.

27. A pharmaceutical aerosol formulation as claimed in claim 26, further comprising a physiologically effective amount of an anticholinergic bronchodilator.

28. A pharmaceutical aerosol formulation as claimed in claim 1, the formulation comprising a physiologically effective amount of each of (a) formoterol, or a salt, ester, solvate, or solvate of a salt or ester thereof; and (b) budesonide, or a salt, ester, solvate, or solvate of a salt or ester thereof.

29. A pharmaceutical aerosol formulation as claimed in claim 1, the formulation comprising a physiologically effective amount of each of (a) formoterol, or a salt, ester, solvate, or solvate of a salt or ester thereof; and (b) mometasone, or a salt ester, solvate, or solvate of a salt or ester therefor.

30. A pharmaceutical aerosol formulation as claimed in claim 1, the formulation comprising a physiologically effective amount of each of (a) formoterol, or a salt, ester, solvate, or solvate of a salt or ester thereof; and (b) fluticasone, or a salt, ester, solvate, or solvate of a salt or ester thereof.

31. A pharmaceutical aerosol formulation as claimed in claim 1, the formulation comprising a physiologically effective amount of each of (a) salmeterol, or a salt, ester, solvate, or solvate of a salt or ester thereof; and (b) fluticasone, or a salt, ester, solvate, or solvate of a salt or ester thereof.

32. The pharmaceutical aerosol formulation as claimed in claim 1, wherein the surfactant is decyl glucoside.

33. The pharmaceutical aerosol formulation as claimed in claim 1, wherein the surfactant is dodecyl maltoside.

34. A pharmaceutical aerosol formulation as claimed in claim 1, the formulation comprising a physiologically effective amount of each of (a) formoterol and (b) budesonide.

35. A pharmaceutical aerosol formulation as claimed in claim 1, wherein the formulation comprises a physiologically effective amount of each of (a) an anticholinergic bronchodilator and (b) a β2-adrenoreceptor agonist.

36. A pharmaceutical aerosol formulation as claimed in claim 1, wherein the formulation comprises a physiologically effective amount of each of (a) an anticholinergic bronchodilator and (b) a glucocorticosteroid.

37. A method for the manufacture of a pharmaceutical aerosol formulation as claimed in claim 1, comprising the steps of:
providing a mixture of the medicament and the surfactant in a vessel;
adding hydrofluoroalkane (HFA) propellant to the vessel; and
mixing the propellant with the medicament/surfactant mixture to produce a medicament/surfactant/propellant mixture in which the medicament and the surfactant are suspended in the propellant as a finely divided powder.

38. The method of claim 37, further comprising the step of mixing additional HFA propellant with the medicament/surfactant/propellant mixture to produce a further mixture in which the medicament and the surfactant are suspended in propellant as a finely divided powder.

39. A method for the treatment of a patient in need of therapy with an inhaled medicament, comprising administering to said patient a therapeutically effective amount of a pharmaceutical aerosol formulation comprising a HFA propellant; a physiologically effective amount of a medicament for inhalation; and an alkyl saccharide surfactant, wherein the medicament and the surfactant are suspended in the propellant as a finely divided powder.

40. The method of claim 39, wherein the formulation comprises a propellant selected from the group consisting of 1,1,1,2-tetrafluoroethane (P134a), 1,1,1,2,3,3,3-heptafluoropropane (P227), and 1,1-difluoroethane (P152a).

41. The method of claim 39, wherein the surfactant is selected from the group consisting of an alkyl glucoside and an alkyl maltoside.

42. The method of claim 39, wherein the medicament is selected from the group consisting of a β2-adrenoreceptor agonist, an anticholinergic bronchodilator, and a glucocorticosteroid.

43. The method of claim 39, wherein the medicament is selected from the group consisting of anti-allergic medicaments, expectorants, mucolytics, antihistamines, cyclooxygenase inhibitors, leukotriene synthesis inhibitors, leukotriene antagonists, phospholipase-A2 (PLA2) inhibitors, platelet aggregating factor (PAF) antagonists, prophylactics of asthma, antiarrhythmic medicaments, tranquilisers, cardiac glycosides, hormones, anti-hypertensive medicaments, antidiabetic medicaments, antiparasitic medicaments, anticancer medicaments, sedatives, analgesic medicaments, antibiotics, antirheumatic medicaments, immunotherapeutic agents, antifungal medicaments, antihypotension medicaments, vaccines, antiviral medicaments, proteins, peptides, vitamins, cell surface receptor blockers, antioxidants, free radical scavengers, and organic salts of N,N'-diacetylcystine.

44. The method of claim 39, wherein the ratio of surfactant to medicament is in the range of 1:50 to 1:0.2.

45. The method of claim 39, wherein the formulation comprises a physiologically effective amount of each of a β2-adrenoreceptor agonist and a glucocorticosteriod.

46. The method of claim 45, wherein the formulation further comprises a physiologically effective amount of an anticholinergic bronchodilator.

47. The method of claim 39, wherein the formulation comprises a physiologically effective amount of each of (a) formoterol, or a salt, ester, solvate, or solvate of a salt or ester thereof; and (b) budesonide, or a salt, ester, solvate, or solvate of a salt or ester thereof.

48. The method of claim 39, wherein the formulation comprises a physiologically effective amount of each of (a) formoterol, or a salt, ester, solvate, or solvate of a salt or ester thereof; and (b) mometasone, or a salt ester, solvate, or solvate of a salt or ester therefor.

49. The method of claim 39, wherein the formulation comprises a physiologically effective amount of each of (a) formoterol, or a salt, ester, solvate, or solvate of a salt or ester thereof; and (b) fluticasone, or a salt, ester, solvate, or solvate of a salt or ester thereof.

50. The method of claim 39, wherein the formulation comprises a physiologically effective amount of each of (a) salmeterol, or a salt, ester, solvate, or solvate of a salt or ester thereof; and (b) fluticasone, or a salt, ester, solvate, or solvate of a salt or ester thereof.

51. The method of claim 39, wherein the formulation comprises a physiologically effective amount of each of (a) formoterol and (b) budesonide.

52. The method of claim 39, wherein the formulation comprises a physiologically effective amount of each of (a) an anticholinergic bronchodilator and (b) a β2-adrenoreceptor agonist.

53. The method of claim 39, wherein the formulation comprises a physiologically effective amount of each of (a) an anticholinergic bronchodilator and (b) a glucocorticosteroid.

* * * * *

UNITED STATES PATENT AND TRADEMARK OFFICE
CERTIFICATE OF CORRECTION

PATENT NO. : 6,932,962 B1
DATED : August 23, 2005
INVENTOR(S) : Kjell G. E. Bäckström It is certified that error appears in the above-identified patent and that said Letters Patent is hereby corrected as shown below:

Title page,
Item [*] Notice, add the following:
-- This patent is subject to a terminal disclaimer. --.
Item [56], References Cited, OTHER PUBLICATIONS,
"Laube et al.," reference, between "Preliminary" and "of" insert -- study --.
"Okumura" reference, replace "acrosol" with -- aerosol --.
Item [57], ABSTRACT,
Line 2, replace "propellant, an" with -- propellant, a --.
Line 3, replace "which is a a" with -- which is a --.

Signed and Sealed this

Twenty-third Day of May, 2006

JON W. DUDAS
*Director of the United States Patent and Trademark Office*